United States Patent [19]

Scott

[11] 4,013,521
[45] Mar. 22, 1977

[54] PROCESS FOR PURIFYING METHANOL BY DISTILLATION

[75] Inventor: Roger Hardiman Scott, Stockton-on-Tees, England

[73] Assignee: Imperial Chemical Industries Limited, London, England

[22] Filed: Jan. 29, 1975

[21] Appl. No.: 545,343

Related U.S. Application Data

[63] Continuation of Ser. No. 389,545, Aug. 20, 1973, abandoned.

[30] Foreign Application Priority Data

Aug. 15, 1973 United Kingdom ............ 39949/73

[52] U.S. Cl. .................................. 203/85; 203/18; 203/99; 203/DIG. 19; 260/643 R
[51] Int. Cl.² ......................................... B01D 3/40
[58] Field of Search ............ 203/99, DIG. 19, 18, 203/19, 83, 85; 260/643 R

[56] References Cited

UNITED STATES PATENTS

| | | | |
|---|---|---|---|
| 3,239,435 | 3/1966 | Conseiller et al. | 260/643 R |
| 3,282,802 | 11/1966 | Clark | 260/643 R |
| 3,293,154 | 12/1966 | Newton | 203/18 |
| 3,391,064 | 7/1968 | Skell | 203/83 |
| 3,406,100 | 10/1968 | Karafian | 203/99 |
| 3,434,937 | 3/1969 | Elliott et al. | 203/83 |
| 3,442,770 | 5/1969 | Wentworth et al. | 203/18 |
| 3,445,345 | 5/1969 | Katzen | 203/99 |

Primary Examiner—Wilbur L. Bascomb, Jr.
Attorney, Agent, or Firm—Cushman, Darby & Cushman

[57] ABSTRACT

Impure methanol containing ethanol is substantially freed of ethanol by distilling a mixture consisting essentially of the impure methanol, ethanol and water with the aid of a distillation column in a region of which the methanol to water ratio is maintained substantially constant, and withdrawing a stream enriched in ethanol from a point near one end of that region.

5 Claims, 1 Drawing Figure

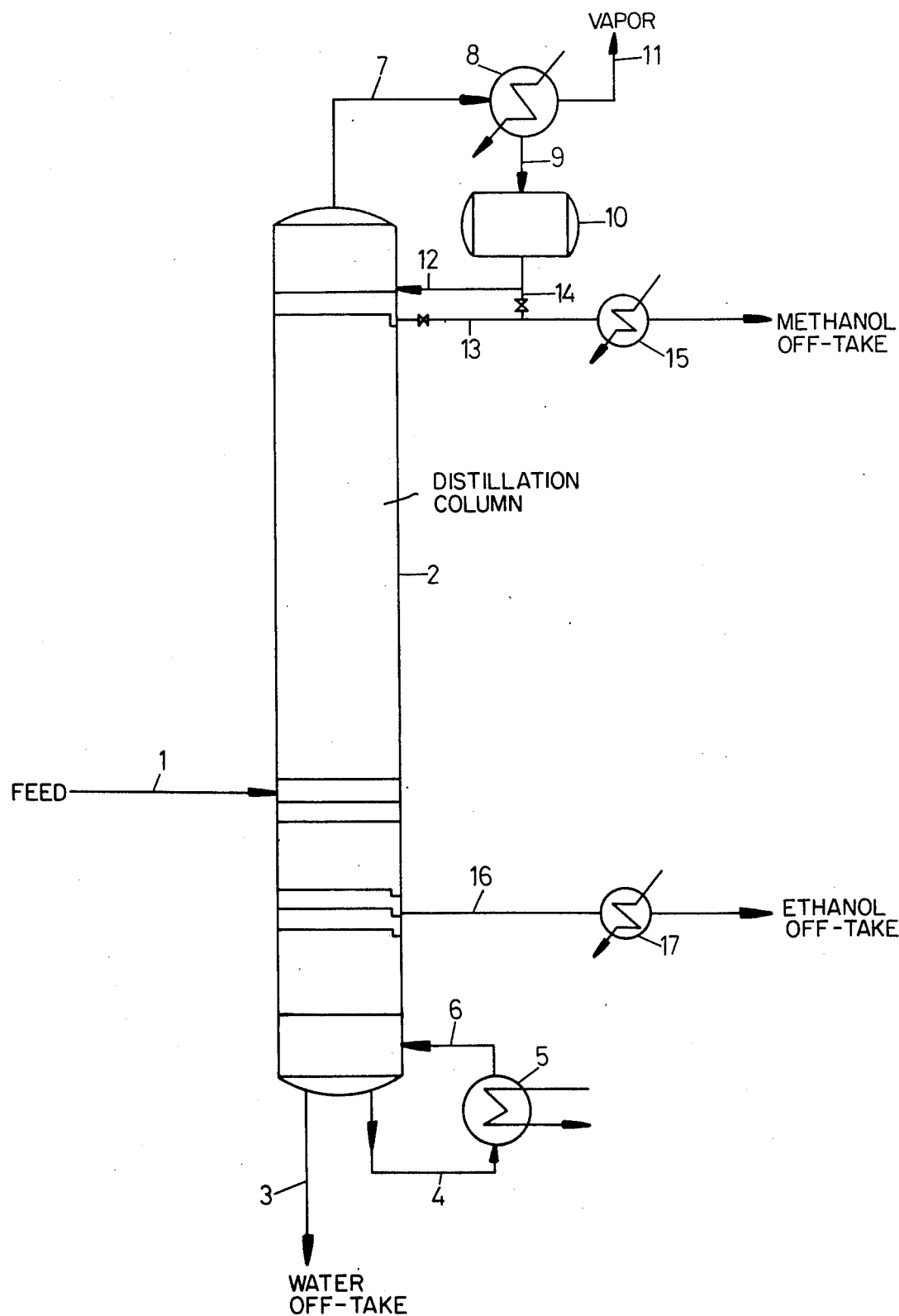

PROCESS FOR PURIFYING METHANOL BY DISTILLATION

This is a continuation, of application Ser. No. 389,545 filed Aug. 20, 1973 and now abandoned. temperature This invention relates to a process of purifying methanol, especially for the removal of small quantities of ethanol from it.

Although modern processes for producing methanol to give rise to a crude product which contains less impurity than older processes at higher temperatures, difficulty is still experienced in removing some organic impurities, particularly ethanol, to the required extent. It has been proposed to effect this by the use of three or more distillation columns operated in series, but this involves the disadvantages of higher capital and running costs as compared with the more usual two-column distillation system. We have now devised a method of operating a distillation column by which methanol of very low ethanol content can be produced in a system normally comprising not more than 2 columns.

According to the invention a mixture consisting essentially of methanol, water and ethanol is distilled with the aid of a distillation column, the methanol to water ratio is maintained substantially constant over a region of the column, and a stream enriched in ethanol is withdrawn from a point near one end of that region.

The enrichment of ethanol occurs because its concentration varies in the normal way along the column, whereas the relative concentration of methanol and water are artificially kept substantially constant. It is possible to carry out the invention by metering a feed of methanol (which should of course be ethanol-free or very low in ethanol) low in the intended ethanol separation region or of water high in the region, or indeed both, but it is most convenient to feed water and methanol containing the ethanol to the column at a point at which, if the column were in equilibrium operation, the water content would be lower than in that mixture. This point could be determined by trail but is more conveniently calculated by known methods from relative volatility data (see for example Robinson et al, "Elements of Fractional Distillation" McGraw-Hill Chapter XIII, page 81 1939). Alternatively the feed could be at a point at which, in equilibrium operation, the methanol content would be lower than in the feed. In either mode of operation a region, known as a "pinch region," is established below the excess-water feed point or above the excess-methanol feed, in which the methanol-water ratio is substantially constant, and the ethanol-enriched stream is withdrawn near the end of the region remote from the feed point of the excess component. If an excess-water pinch region is employed, the ethanol-enriched stream is withdrawn preferably from the liquid present at a level below the feed point. If an excess-methanol pinch region is employed, the ethanol-enriched stream is withdrawn preferably from the vapour present at a level above the feed point. In order to produce methanol of low ethanol content it is more efficient to use an excess-water pinch region alone.

The point at which the ethanol-enriched stream is withdrawn is preferably just outside the pinch region since it is found that the ethanol content increases further between the boundary of the pinch region and the point at which (for an excess-water pinch region) the methanol mole fraction is about 0.5. Thus the withdrawal point is preferably between the end of the pinch region and the point at which the methanol mole fraction is 0.4. The composition and/or temperature of the ethanol-enriched stream is preferably continuously measured and the imputs to the column, especially the re-boiler heating rate, are controlled in response thereto to stabilize the composition of that stream at the required, usually the highest possible, ethanol content.

The proportion of ethanol which occurs in synthetic crude methanol is normally up to 0.3, more rarely up to 0.5% $w/w$. Distillation according to the invention is capable of decreasing this to 20 ppm $w/w$ or even lower, for example 10 ppm $w/w$, according to the length of the pinch region. A region of 10–20% of the column length, for example 6 to 24 plates in a column of total height 60 to 120 plates is of general applicability.

The feed to the distillation according to the invention preferably contains under 50%, especially 8–30%, of water by weight. Discarded water or product methanol or both can be recycled in order to maintain the feed composition within the desired limits and can be added to the feed or fed separately to the column.

The feed to the distillation is preferably the product of a preliminary distillation in which a crude methanol is substantially freed from components boiling at below the boiling point of methanol. Thus a 2-column system suffices to remove both the low-boiling components and the ethanol. Such a system is usually adequate when the crude methanol has been derived from a synthesis process operated at under 300° C, for example 190–270° C, such that only a small quantity of higher-boiling impurity is present.

When the crude methanol is derived from a synthesis process operated at above 300+ C or there are reasons for requiring a very pure product methanol, the distillation according to the invention can be preceded by a water-extractive distillation, producing a methanol stream of very high water content, for example 40 to 60% water or even 80 to 95% water. In this event it is preferred to employ an intermediate column in which a coarse separation of methanol and water is effected and a stream containing the preferred proportion of methanol is produced.

Since the process requires a longer column than simple distillation, the heat consumption (for an excess-water process) is higher than has been usual, but not so high as to outweigh the savings in capital and running costs due to having only two columns or two main and one simple column. A typical heat consumption is 650–1050 metric ton calories per metric ton of refined methanol, more usually 780–910, depending on the ethanol level in the crude methanol, the degree of purification required, the water content of the crude methanol, the number of plates in the column being as described above. Correspondingly the boiling rate of the reboiler section of the column is suitably from 1.6 to 2.2 times the feed rate to the column, which is commonly in the range 1.1 to 1.6 for distillation without the pinch region. The re-boiler and reflux ratios are correspondingly greater. The boiling rate is, of course, less than would bring the column to a state of equilibrium, since a pinch-region would then not be present. Analogous considerations apply to an excess-methanol process.

Since distillation according to the invention permits ethanol to be inexpensively removed, it follows that constraints applied to the synthesis process with a view to minimising ethanol formation need be less severe. In particular, in addition to the normally used temperature range 210–270° C, temperatures up to 300° C become readily usable; and as a consequence the life of catalysts containing copper, and oxides such as those of zinc, aluminium, chromium, manganese, vanadium and mixtures thereof is effectively lengthened, since such catalysts need be discharged only when their activity has declined to the point at which a temperature of 300° C is required, not at the earlier time when the up to now preferred temperature of 270° C is needed. Likewise, production rates correspondingly can be higher.

The distillation according to the invention is preferably used in conjunction with a process as described in our UK Pat. specifications Nos. 1010871 and 1159035, the subject-matter of which is incorporated herein by reference. Analogous processes using other copper-containing catalysts or employing synthesis in conditions of indirect heat exchange are also suitable.

The accompanying drawing shows diagrammatically a methanol refining column according to the invention. Where trays are referred to by number, the numbering is from the bottom upwards.

In the column 2, which contains 76 trays of which, for clarity, only 9 are shown, point 1 is the feed point (between trays 10 and 40), point 3 is the water off-take, point 13 or 14 the product methanol off-take with cooler 15, point 11 the vapour purge off-take and point 16 the ethanol off-take with cooler 17. The column includes a re-boiler steam-heated at 5, fed with liquid by pipe 4 and delivering vapour through pipe 6. At the top the column has a reflux system including vapour off-take 7, partial condenser 8, vapour purge off-take 11, liquid condensate return pipe 9 with reflux storage drum 10 and condensate column feed 12. An optional product methanol off-take 13 from plate 74 is provided as an alternative to off-take 14 from drum 10. The vapour purge 11 may lead to means for recovering methanol from it, suitably to the overhead system of the topping column if one is used. The column also includes means not shown for measuring the composition and/or temperature of the stream leaving at 16 and to control the rate at which steam is supplied to the re-boiler at 5.

The drawing shows an indirectly-heated re-boiler, but live steam can be used if desired, provided it is available in a pure enough state.

In the operation of the column a crude methanol (59.37 tonne/hour, 80.3% methanol $^w/w$) derived from synthesis at 50 atmospheres pressure over a copper-zinc oxide-alumina catalyst, from which low-boiling impurities had been removed in a topping column, was fed at its boiling point 87° C to the column at point 1, which was tray 24. From the top of the column a stream of vapour was taken at 7 (142.2 tonne/hour) and returned (apart from a product stream — see below — and a vapour purge of 0.24 tonne/hour) to the column as reflux at 12. A product methanol stream (99.96% $^w/w$, 46.1 tonne/hour) was withdrawn either from the third-from-top-plate at 13, or from the reflux circuit. The reflux ratio (weight of methanol returned÷weight of methanol leaving) was 2.07. Below the feed tray the methanol proportion remained substantially constant down to and including tray 14. A liquid ethanol-enriched stream (1.3 tonnes/hour) was withdrawn at 16 (at tray 9, taking from the downcomer pipe from tray 10) having the composition methanol 57.5%, water 35.6%, higher alcohols 4.5% and ethanol 2.4%, all by weight. At the bottom of the column a water stream (11.74 tonne/hour) was withdrawn at 3 and 71.15 tonne/hour of water was re-boiled and fed in at 6. The re-boiler rate (weight of material returned in the column÷weight of material leaving) was 7.0. The rate of feed of steam to the reboiler was 72.5 tonne/hour at 144.5° C and 45 psig; indirect heat exchange was employed.

The compositions of the liquid at the trays in and below the feed tray were as shown in the Table.

| Tray no. | $\%^w/w$ methanol | $\%^w/w$ ethanol |
| --- | --- | --- |
| 9 | 63 | 2.41 |
| 10 | 70 | 2.76 |
| 11 | 75 | 2.74 |
| 12 | 79 | 2.54 |
| 14 | 83 | 1.98 |
| 16 | 85 | 1.58 |
| 18 | 85.5 | 1.18 |
| 20 | 86 | 0.86 |
| 22 | 86 | 0.64 |
| 24(feed) | 86 | 0.45 |

It is evident that the methanol mole fraction is substantially constant for 9 trays below and including the feed tray (16–24) and that the ethanol concentration is highest in the liquid about 9 trays below the bottom of the pinch region occupying trays 16-24.

I claim:
1. A process for purifying methanol from a starting mixture of synthetic crude methanol consisting essentially of methanol, 8 to 30% by weight water and up to 0.5% by weight ethanol comprising:
   a. feeding said starting mixture to a distillation column at a level which when said column is in equilibrium operation, the water content within said column at said level is lower than in said mixture producing over a region of the column below the feed level a substantially constant methanol to water weight ratio,
   b. withdrawing water as bottoms,
   c. withdrawing product methanol from the upper part of the column, and
   d. withdrawing a side stream enriched in ethanol from a level below the end of the region remote from the feed level.
2. A process according to claim 1 in which the ethanol enriched stream is withdrawn at the point at which the methanol mole fraction is 0.4.
3. A process according to claim 1 wherein said region occupies 10 to 20% of the length of the column.
4. A process for purifying methanol from a starting mixture of synthetic crude methanol comprising:
   a. subjecting a crude methanol mixture to water extractive distillation and removing a methanol-containing stream as bottoms:
   b. subjecting said methanol containing stream as bottoms to a coarse distillation separation of methanol wherein the methanol containing stream is collected overhead to produce a starting mixture consisting essentially of methanol, 8 to 30% by weight water and up to 0.5% by weight ethanol;

c. feeding said starting mixture to a distillation column at a level which when said column is in equilibrium operation, the water content is lower within said column at said level than in said mixture producing over a region of the column below the feed level a substantially constant methanol to water weight ratio;

d. withdrawing water as bottoms, e. withdrawing product methanol from the upper part of the column, and f. withdrawing a side stream enriched in ethanol from a level below the end of the region remote from the feed level.

5. A process for producing purified methanol comprising:

a. subjecting a crude methanol mixture containing as impurities water, ethanol and low boiling impurities to a distillation in which said mixture is freed of components boiling at a the boiling point of methanol to produce a starting mixture of methanol, 8 to 30% by weight water and up to 0.5% ethanol;

b. feeding said starting mixture to a distillation column at a level which when said column is in equilibrium operation, the water content is lower within said column at said level than in said mixture producing over a region of the column below the feed level a substantially constant methanol to water weight ratio;

c. withdrawing water as bottoms, d. withdrawing product methanol from the upper part of the column, and e. withdrawing a side stream enriched in ethanol from a level below the end of the region remote from the feed level.

* * * * *